(12) United States Patent
Epstein

(10) Patent No.: US 6,613,043 B2
(45) Date of Patent: Sep. 2, 2003

(54) SYSTEM FOR INCREASING THE ACCURACY AND SAFETY OF ABLATIVE LASER TREATMENTS

(76) Inventor: Robert L. Epstein, 5400 W. Elm St., McHenry, IL (US) 60050

( * ) Notice: Subject to any disclaimer, the term of this patent is extended or adjusted under 35 U.S.C. 154(b) by 147 days.

(21) Appl. No.: 09/992,152

(22) Filed: Nov. 6, 2001

(65) Prior Publication Data

US 2003/0084908 A1 May 8, 2003

(51) Int. Cl.[7] .............................................. A61F 9/007
(52) U.S. Cl. ............................. 606/10; 606/3; 606/5; 606/12
(58) Field of Search .......................... 606/2, 5, 10–14

(56) References Cited

U.S. PATENT DOCUMENTS

| 5,613,965 A | | 3/1997 | Muller | |
|---|---|---|---|---|
| 5,741,245 A | * | 4/1998 | Cozean et al. | 606/10 |
| 5,919,186 A | | 7/1999 | Bath | |
| 6,063,072 A | | 5/2000 | Muller | |
| 6,344,040 B1 | * | 2/2002 | Juhasz et al. | 606/5 |

OTHER PUBLICATIONS

Maddox, B., Photorefractive Keratectomy (PRK) for the Correction of Myopia, Hyperopia, and Astigmatism using the Summit Technology Argon–Fluoride Excimer Laser, Nov. 1996.

* cited by examiner

Primary Examiner—David M. Shay
(74) Attorney, Agent, or Firm—George H. Gerstman; Seyfarth Shaw

(57) ABSTRACT

A method and apparatus are provided to increase the accuracy and safety of ablative laser treatments of the eye. In an illustrative embodiment, tissue is removed from the cornea, via a laser, to provide an effluent from the cornea. The effluent is aspirated and deposited into a chemical analyzer. The amount of effluent that has been deposited is quantitated. Data relating to a dimension of the ablated cornea is inputted to a computer and data relating to the quantitized effluent is also inputted to the computer. The computer uses the quantitized effluent data and the inputted dimension data to estimate the number of diopters of treatment accomplished. The estimated number of diopters of treatment accomplished is compared to a desired number of diopters of treatment and the laser treatment is modified based on the comparison for most accurate optical results.

23 Claims, 4 Drawing Sheets

SYSTEM FOR INCREASING THE ACCURACY AND SAFETY OF ABLATIVE LASER TREATMENTS

FIELD OF THE INVENTION

The present invention concerns a novel method and apparatus for surgically removing tissue from the cornea of an eye using an ablative laser, in which the accuracy and safety of the treatment is increased.

BACKGROUND OF THE INVENTION

Ablative laser treatments occur in several areas in medicine including cosmetic laser skin resurfacing and excimer laser vision correction.

LASIK is a currently popular outpatient vision correcting excimer laser surgical procedure in which an excimer laser is used to remove tissue from the human cornea to change its shape. Each excimer laser pulse causes a photochemical reaction that sputters off a plume containing small amount of tissue. PRK and LASEK are variations of LASIK and all these procedures cause removal of microscopic amounts of tissue from the human cornea.

The laser treatment to correct myopia removes a disc shaped section of cornea. The disc has a prescribed diameter based on the settings of the laser. The thickness of the tissue removed is greater in the center of the disc and thinner toward the periphery. Another laser treatment known as phototherapeutic keratectomy or PTK is used to remove lesions and to change eye optics. In these laser treatments, an amount of the cornea tissue is removed to achieve the beneficial result.

To a large extent, inaccuracy in LASIK correction results from the variable response of corneal tissue to ablation by the laser. Because of the variable response, it is commonly necessary to reoperate to adjust for undercorrections or overcorrections. Many factors affect the actual amount of tissue removed including atmospheric humidity and pressure, patient age, variations in hormonal level, the variations in timing by different surgeons on different patients allowing a variable amount of tissue drying during the procedure, etc. Experienced surgeons can perform statistical studies on their data and can become more uniform in their procedures, but there is always some degree of patient-to-patient variation.

The material removed from the cornea during an excimer laser ablation is somewhat toxic to the surgical personnel in that the surgical personnel may breathe in aerosolized protein from another human. The protein may cause allergic reactions in the respiratory system. More seriously, the protein sputtered off the cornea of a patient could possibly carry viral particles and very tiny prions such as transmit hepatitis, Creutzfeld-Jakob disease (human "mad cow" disease), and possibly human immunodeficiency virus (which causes AIDS).

There are several methods to guard the surgeon against disease transmission including methods as simple as breathing through a snorkel tube to more involved methods which aspirate the material as it is sputtered off the cornea in the surgery. The problem with the devices that aspirate away particles is that moving air can introduce a drying action on the cornea and cause further inaccuracy to the laser treatment. However, aspiration of tissue removed from the cornea during surgery has been found effective to alleviate the potentially toxic reactions and also to alleviate the offensive odor that is common with laser surgery.

It is an object of the invention to provide a system for increasing the accuracy of ablative laser treatment of the cornea.

Another object of the present invention is to provide a system for analyzing removed living tissue during a laser ablation.

A further object of the invention is to provide a system for optimizing laser treatment of the human cornea using aspiration of the removed living tissue and quantitative analysis of the aspirated tissue.

A still further object of the present invention is to provide a system for surgically removing tissue from the cornea of an eye during an ablative laser treatment, which is simple to operate yet enables increased accuracy of ablative laser treatment.

Other objects and advantages of the present invention will become apparent as the description proceeds.

BRIEF DESCRIPTION OF THE INVENTION

In accordance with one embodiment of the present invention, a method is provided for increasing the accuracy and safety of ablative laser treatments of the eye. An amount of tissue is removed from the cornea, using an ablative laser, thereby providing an effluent. The effluent is aspirated and quantitized. An estimated* actual optical change is computed, based upon input data relating to a dimension of the ablative cornea and the quantitized effluent. The estimated actual optical change is compared to a desired optical change, and the laser treatment is modified based upon the comparison of the estimated actual optical change to the desired optical change.

*The results of the computations are referred to herein as "estimated" because of inherent imperfections in the effluent aspiration.

In the illustrative embodiment, the input data relating to the dimension of the ablative cornea includes at least one of the radius, diameter, area and periphery of the ablated cornea. The estimated actual optical change is computed by a computer which may use various algorithms, including but not limited to the Munnerlyn formula.

In another embodiment of the present invention, an amount of tissue is removed from the cornea using an ablative laser, thereby providing an effluent. The effluent is aspirated and quantitized, and an estimated depth of tissue removed is computed based upon input data relating to a dimension of the ablated cornea and the quantitized effluent. The estimated depth of tissue removed is compared to a desired depth of tissue to be removed and the laser treatment is modified, based upon the comparison of the estimated actual depth of tissue removed to the desired depth of tissue to be removed.

In accordance with one embodiment of the present invention, an apparatus is provided for increasing the accuracy and safety of ablative laser treatments of the eye. The apparatus includes an ablative laser, an aspirator for aspirating the effluent from the cornea, a chemical analyzer for quantitating the amount of effluent that has been aspirated from the cornea, and a computer for receiving data relating to a dimension of the ablative cornea and for receiving the quantitized effluent collected.

In one embodiment of the invention, the computer is operative to estimate the actual optical change (number of diopters of treatment accomplished) based on the inputted dimension data and the quantitized effluent data. The estimated actual optical change is compared with a desired optical change to provide information to the operator (surgeon) to allow for further corrective action at the time of the original operation for the sake of greater accuracy of treatment.

In another embodiment, the computer is operative to estimate the depth of ablative tissue based on the inputted dimension data and the quantitized effluent data. The estimated depth of ablative tissue is compared with a desired depth of tissue to be ablated to provide information to the operator (surgeon) to allow for further corrective action for the sake of greater accuracy of treatment.

In the illustrative embodiment, the effluent is quantitated in a chemical analyzer and the input data relating to the size of the ablated cornea comprises input data relating to at least one of the radius, diameter, area, and periphery of the ablated cornea.

A more detailed explanation of the invention is provided in the following description and claims, and is illustrated in the accompanying drawings.

DETAILED DESCRIPTION OF THE ILLUSTRATIVE EMBODIMENTS

Figure 1:
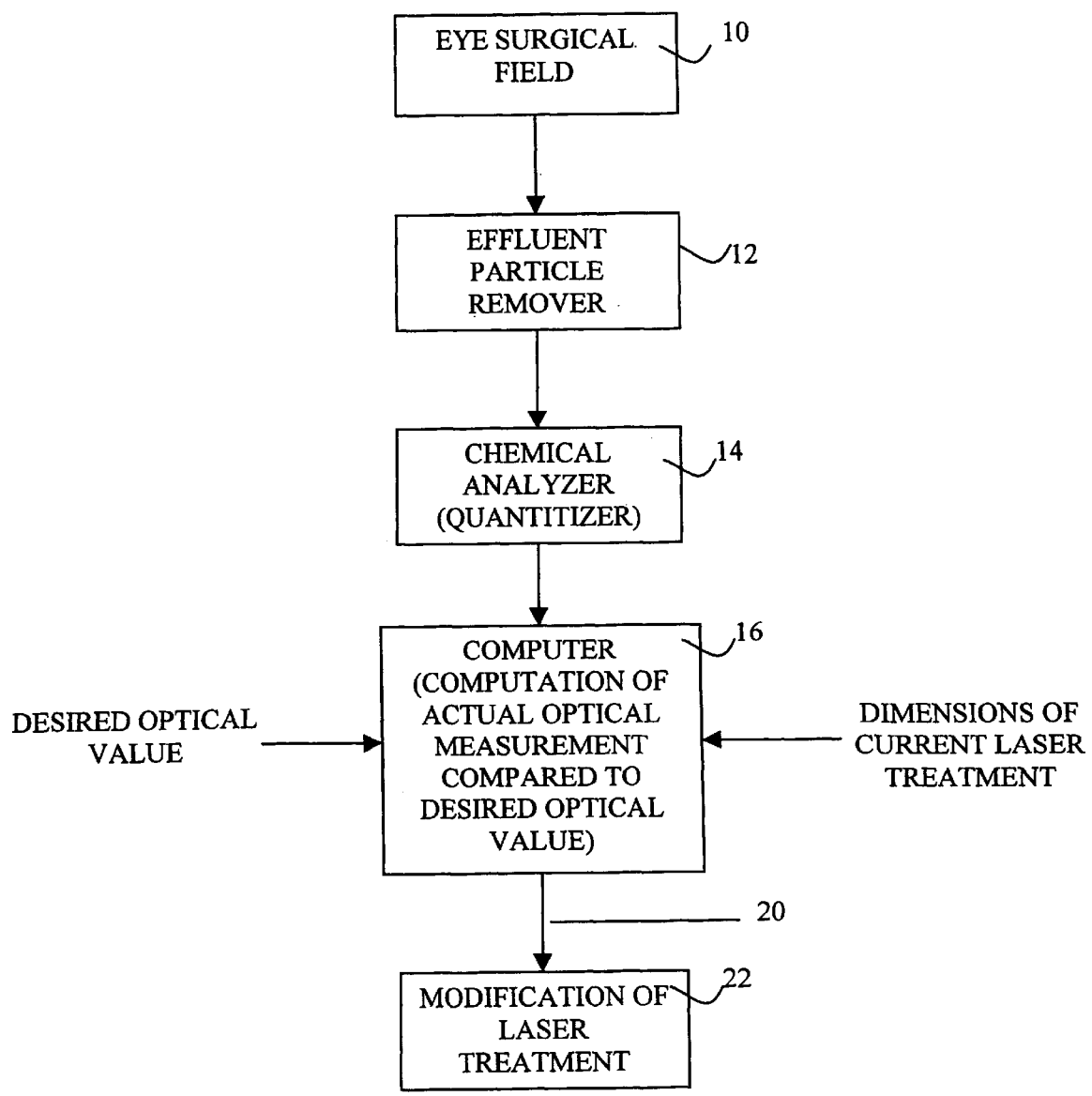
FIG. 1 is a diagram of an apparatus for surgically removing tissue from the cornea of an eye, in accordance with an embodiment of the present invention.

The system of the present invention includes an excimer laser, which is well known in the art for removing tissue from the cornea. Referring to FIG. 1, the excimer laser is used within eye surgical field 10. During laser treatment of the patient's eye, a plume of hydrocarbons is removed from the eye surgical field using an effluent particle remover 12. Although no limitation is intended, a specific example of an effluent particle remover that could be used with the present invention is the Laser Clean Room System™ sold by Mastel Precision, Inc., Rapid City, S. Dak. The effluent particle remover 12 removes airborne particles including hydrocarbons which are by-products of the ablation. It is desired that all of the effluent from the cornea that occurs during the excimer laser operation be aspirated by the effluent particle remover.

A chemical analyzer 14 quantitates the effluent. The chemical analyzer may be a protein analyzer, a total hydrocarbon analyzer or any other suitable analyzer for quantitating the amount of material that has emanated from the treated cornea. As a specific example although no limitation is intended, the chemical analyzer 14 used for the present invention may be a Sargent-Welch brand CERA™ Gas Chromatograph 100, manufactured by Sargent-Welch, Buffalo Grove, Ill.

The output signal from chemical analyzer 14, containing data relating to the quantitated effluent, is fed to a computer 16. Preferably, this output indicates the weight (W) of the ablated tissue in micrograms. The operator also inputs into computer 16 data concerning one or more of the dimensions of the current laser treatment, for example the diameter of the optical zone of ablation (S). The operator also inputs to the computer the desired optical value, for example, the number of diopters change that is desired as a result of the laser treatment.

Computer 16 estimates the actual optical change that has occurred. In a specific example in which the ablation into the cornea is a parabolic cone, although no limitation is intended, using the Munnerlyn formula, the actual optical measurement (D) i.e., the number of diopters of optical correction that has occurred, is derived.

For typical excimer laser ablation for correction of myopia, the shape of the ablation is a parabolic cone. The greatest ablation is at the center of the cone.

Per diopter of optical change, the greatest ablation depth $Z_o$ is given by the Munnerlyn formula:

$$Z_0 = \frac{KS^2}{3} \qquad (1)$$

S is the size of the optical zone diameter,
and K=1 micron/mm$^2$, a dimensional constant.

Figure 4:
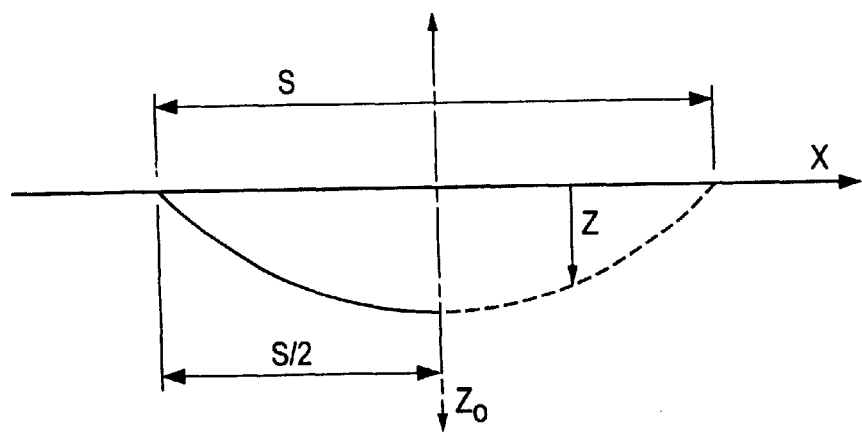
FIG. 4 is a graphical representation of an ablated area.

In cross-section through the optical zone center, the ablation is a parabola. Refer to FIG. 4 which shows the representation of an ablated area. The ablation depth at point X distance away from the optical center is given by the formula $Z=Z_0-MX^2$. At X=s/2 there is no ablation at Z=0. (2)

Also $Z=Z_0-M(S/2)^2=0$ when X=S/2 (3)

Therefore, $M=4Z_0/S^2$, or substituting from (1) (4)

$$M = \frac{4KS^2}{3S^2} = \frac{4K}{3} \qquad (5)$$

Thus, the equation for the cross-section is given by $Z=Z_0-{}^4/_3KX^2$ (6)

Figure 5:
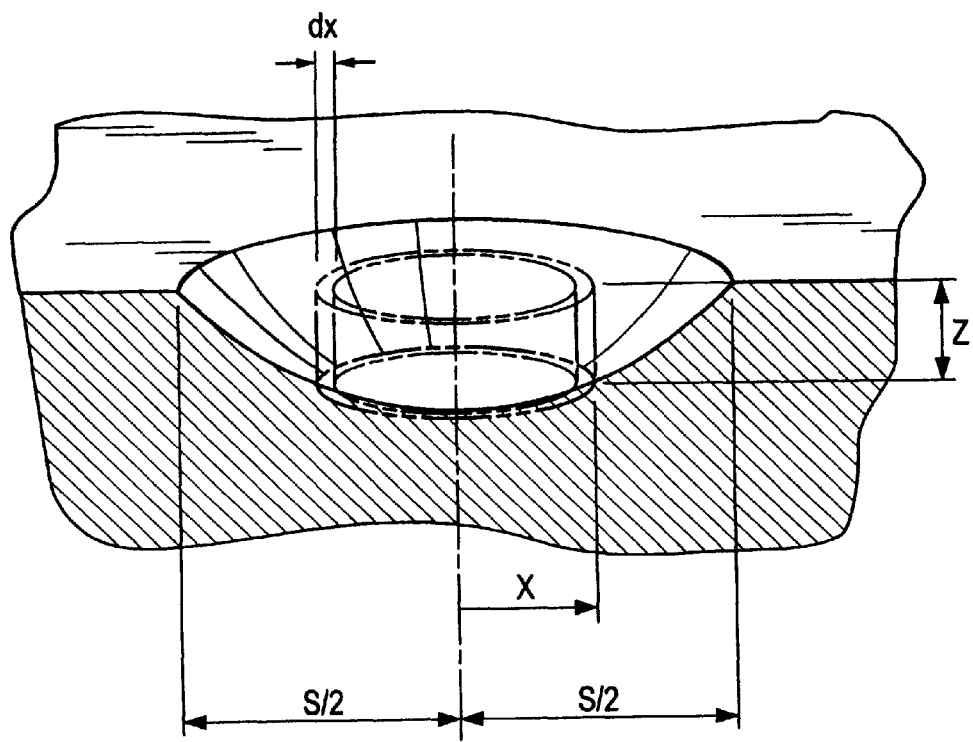
FIG. 5 is a graphical representation of a parabolic cross-section of ablation and a circular cylinder.

The volume of the ablated parabolic cone can be calculated as the summation of the volumes of the walls of circular cylinders of height Z, radius X and thickness dx, with reference to FIG. 5 which is a representation of the parabolic cross-section of ablation and a circular cylinder. Thus, the volume of corneal tissue ablated per diopter is given by $Z=Z_0-{}^4/_3KX^2$ $$V = \int_0^{\frac{S}{2}} 2\pi X Z d_X = 2\pi \int_0^{\frac{S}{2}} X\left(Z_0 - \frac{4K}{3}X^2\right)d_x$$

$$= 2\pi \int_0^{\frac{S}{2}} \left(Z_0 X - \frac{4K}{3}X^3\right)d_x$$

$$= 2\pi \left[\left(\frac{Z_0}{2}X^2 - \frac{KX^4}{3}\right)\right]_0^{S/2}$$

But by (1)

$$Z_0 = \frac{KS^2}{3},$$

so $$V = 2\pi\left[\frac{Z_0}{2}\left(\frac{S}{2}\right)^2 - \frac{K}{3}\left(\frac{S}{2}\right)^4\right]$$

$$= 2\pi\left(\frac{KS^2}{6}\cdot\frac{S^2}{4} - \frac{KS^4}{48}\right)$$

$$= \frac{K\pi S^4}{24}$$

cubic millimeters per diopter of optic change.

For example, if the optical zone size (or diameter) of the laser ablation is 6.5 mm, then $$V = \frac{\pi \times (6.5)^4}{24} \times \frac{1\text{ micron}}{\text{mm}^2} \times \text{mm}^4$$

$$= \frac{1785\pi}{24} \times 10^{-3}\text{ mm}^3$$

$$= 233.5 \times 10^{-3}\text{ mm}^3$$

$$= .234\text{ mm}^3\text{ of volume ablated}$$

The dry weight of a cut corneal button 10.5 mm in diameter, 0.525 mm in the center and 0.700 mm in the periphery, was found to be 83 mg.

Assuming an average cornea (thickness of 625 microns, the corneal volume of the cut section is $\pi r^2 \times \text{thickness} = \pi r (5.25)^2 \times 0.625\text{ mm}^3 = 54\text{ mm}^3$.

The cornea weighs $$\frac{83 \times 10^{-3}\text{ grams}}{54 \times 10^{-3}\text{ cm}^3} = 1.54\text{ grams/cm}^3$$

and therefore, the weight W of a diopter of ablated cornea is $1.54 \times 1.17 \times 10^{-4}$ grams for 18 mg/diopter W=18 micrograms/diopter The collected and processed tissue will be a certain proportion P of the total tissue removed by laser.

As an example, although no limitation is intended, 18 P micrograms per diopter is collected where P is likely to be between 0.95 and 1.0 and depends on the specifics of the laser machinery configuration. It can be seen that by knowing the value of S, which is the optical zone size, W, which is the weight of collected tissue, and P, which is the portion of material collected, one can predict the optical change induced to the eye by the formula: Diopters=W(in micrograms)/18P.

D, which is represented by the output 20 of computer 16, is preferably expressed in diopters of actual optical correction. This guides the surgeon to add or subtract optical correction with the laser (represented by box 22 in FIG. 1). Output 20 may be fed via an automated link to the treating laser, to automatically modify the laser treatment by optimizing laser correction for greatest accuracy based upon the comparison of the estimated actual optical measurement to the desired optical value.

Figure 2:
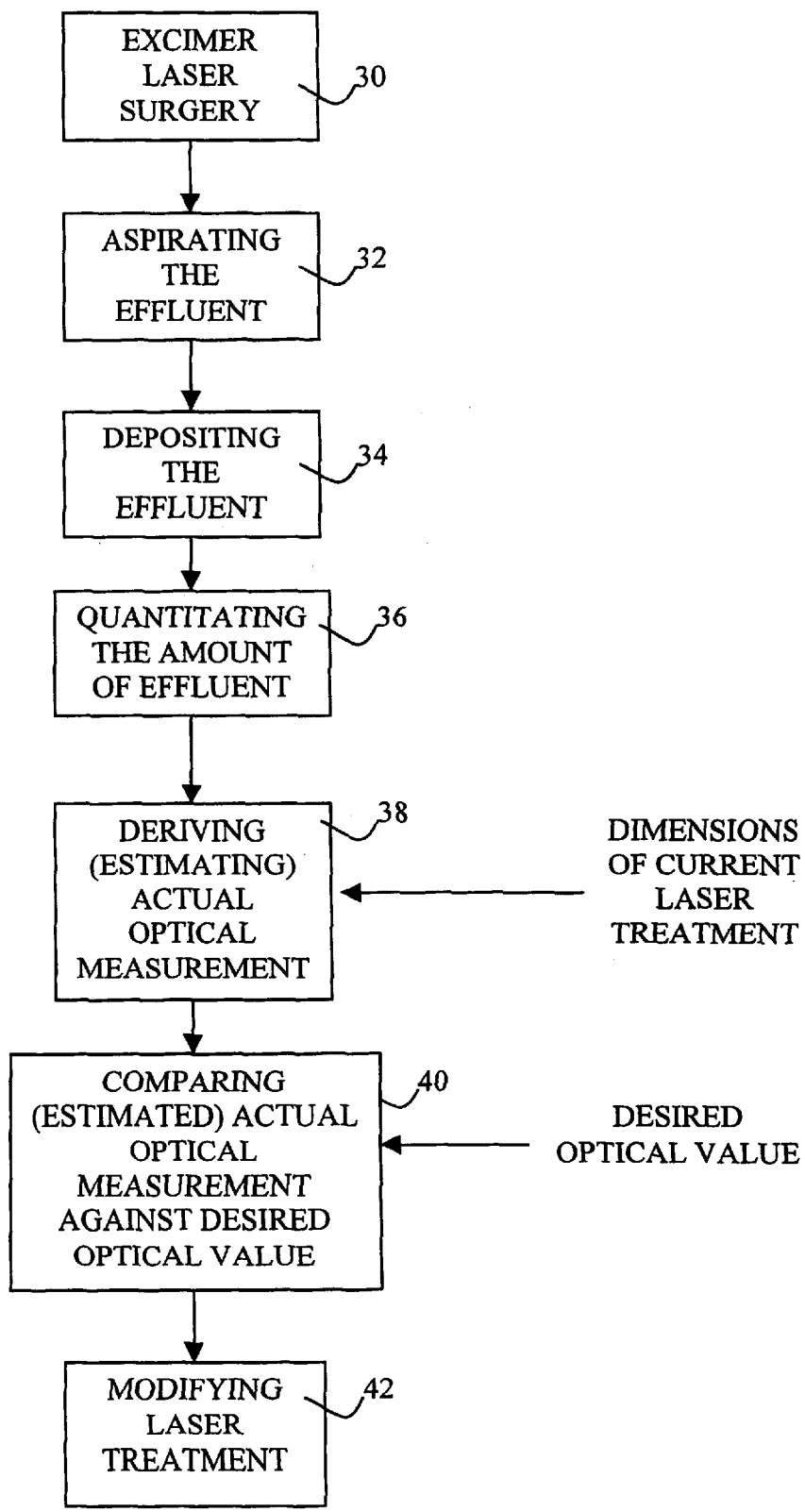
FIG. 2 is a flow chart showing a method for surgically removing tissue from the cornea of an eye, in accordance with an embodiment of the present invention.

A method according to one embodiment of the present invention is illustrated in the flow diagram of FIG. 2. Referring to FIG. 2, the surgeon performs excimer laser surgery 30 and the effluent is aspirated. The aspirated effluent is deposited 34 and is quantitated 36. Dimensions of the current laser treatment, such as the radius, diameter, area, or periphery of the ablated cornea are used to derive an actual optical measurement 38 in the form of number of diopters treated. The actual optical measurement is compared against the desired optical value (box 40) and the laser treatment is modified based upon this comparison (box 42). As stated above, such modification may be by automatic linkage to the ablation laser.

In using the system of the present invention, a surgeon has the ability to perform a "test dose" of the excimer laser to determine at the beginning of surgery whether the patient is likely to be undercorrected or overcorrected by the standard laser treatment. After the laser treatment, the surgeon has the option to add further laser correction in the same operative setting based upon the computation of the actual optical measurement resulting from the information provided by the chemical analyzer and the dimensions of the optical treatment.

Figure 3:
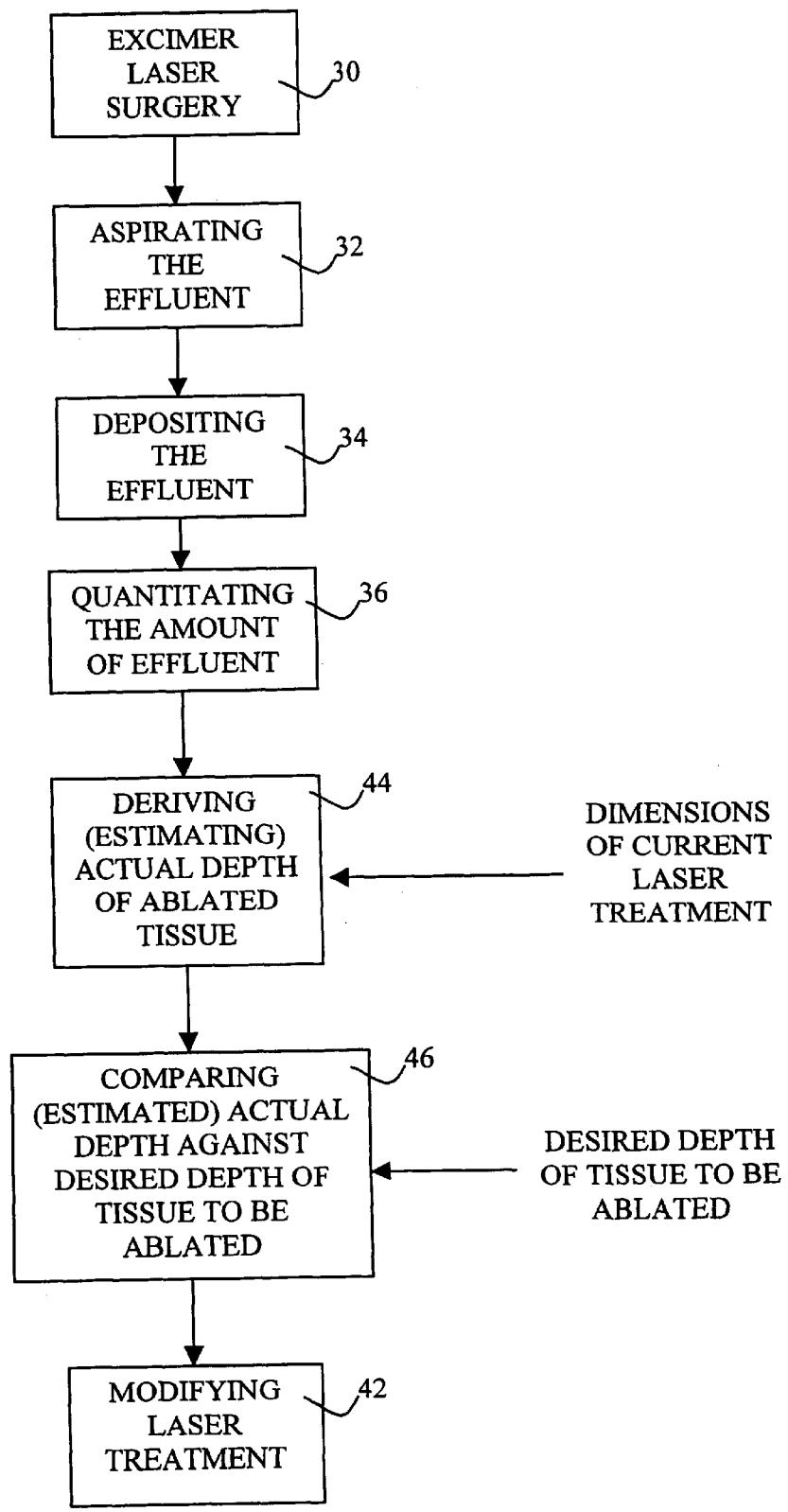
FIG. 3 is a flowchart showing a method for surgically removing tissue from the cornea of an eye, in accordance with another embodiment of the present invention.

A method according to another embodiment of the present invention is illustrated in the flow diagram of FIG. 3. Referring to FIG. 3, the surgeon performs an excimer laser surgery 30 and the effluent is aspirated. The aspirated effluent is deposited 34 and is quantitated 36. A dimension of the current laser treatment, such as the area, is used to derive an estimated actual depth measurement 44 which is the estimated depth of the tissue that has been ablated. The estimated actual depth of tissue that has been ablated is compared against the desired depth of tissue to be ablated (box 46) and the laser treatment is modified based upon this comparison (box 42). Such modification may be made by automatic linkage to the ablation laser.

It can be seen that a novel method and system have been provided that increases the accuracy of ablated laser treatment of the cornea and alleviates potentially toxic reactions and the offensive odor that is common with laser surgery. Although illustrative embodiments of the invention have been shown and described, it is to be understood that various modifications and substitutions may be made by those skilled in the art without departing from the novel spirit and scope of the present invention.

What is claimed is:

1. An apparatus for increasing the accuracy and safety of ablative laser treatments of the eye, which comprises:
    an ablative laser;
    an aspirator for aspirating the effluent from the cornea; and
    a chemical analyzer for quantitating the amount of effluent that has been aspirated from the cornea, whereby data concerning the quantitized effluent collected can aid in computing an estimated actual optical change or in computing the estimated depth of the ablated tissue accomplished.

2. An apparatus for increasing the accuracy and safety of ablative laser treatments, which comprises:
    an ablative laser;
    an aspirator for aspirating the effluent from the cornea;
    a chemical analyzer for quantitating the amount of effluent that has been aspirated from the cornea;
    a computer for receiving data relating to a dimension of the ablated cornea and for receiving data concerning the quantitized effluent collected, said computer being operative to estimate the number of diopters of treatment accomplished based on said inputted dimension data and said quantitized effluent data.

3. An apparatus as defined in claim 2, in which said chemical analyzer is a gas chromatograph.

4. An apparatus as defined in claim 2, in which said computer is programmed to derive the number of diopters of treatment accomplished using an algorithm relating to the Munnerlyn formula.

5. An apparatus for increasing the accuracy and safety of ablative laser treatments of the eye, which comprises:

an ablative laser;

an aspirator for aspirating the effluent from the cornea;

a chemical analyzer for quantitating the amount of effluent that has been aspirated from the cornea;

a computer for receiving data relating to a dimension of the ablated cornea and for receiving data concerning the quantitized effluent collected, said computer being operative to estimate the depth of the ablated tissue accomplished based on said inputted dimension data and said quantitized effluent data.

6. An apparatus as defined in claim 5, in which said chemical analyzer is a gas chromatograph.

7. A method for increasing the accuracy and safety of ablative laser treatments, comprising the steps of:

providing an ablative laser;

removing an amount of tissue from the cornea, using the ablative laser, thereby providing an effluent;

aspirating the effluent; and quantitizing the effluent;

whereby said quantitized effluent collected can aid in computing an estimated actual optical change or in computing the estimated depth of the ablated tissue accomplished.

8. A method for increasing the accuracy and safety of ablative laser treatments, comprising the steps of:

removing an amount of tissue from the cornea via an excimer laser to provide an effluent from the cornea;

aspirating the effluent from the cornea;

depositing the aspirated effluent into a chemical analyzer;

using the chemical analyzer to quantitate the amount of effluent that has been deposited;

inputting data to a computer relating to a dimension of the ablated cornea and the quantitated effluent; and via the computer, using the quantitized effluent data and the inputted dimension data to estimate the depth of ablated tissue.

9. A method as defined in claim 8, including the step of comparing the estimated depth of ablated tissue to a desired depth of tissue to be ablated.

10. A method as defined in claim 9, including the step of modifying the laser surgery based upon the computation of estimated depth of ablated tissue compared to the desired depth of tissue to be ablated.

11. A method for increasing the accuracy and safety of ablative laser treatments, comprising the steps of:

removing an amount of tissue from the cornea via an excimer laser to provide an effluent from the cornea;

aspirating the effluent from the cornea;

depositing the aspirated effluent into a chemical analyzer;

quantitating the amount of effluent that has been deposited;

inputting data to a computer relating to a dimension of the ablated cornea and the quantitized effluent; and via the computer, using the quantitized effluent data and the inputted dimension data to estimate the number of diopters of treatment accomplished.

12. A method as defined in claim 11, in which the dimension data inputted into the computer comprises at least one of the radius, diameter, area, and periphery of the ablated cornea.

13. A method as defined in claim 11, in which the computer estimates the number of diopters of treatment accomplished using an algorithm based upon the Munnerlyn formula.

14. A method as defined in claim 11, in which the aspirated effluent is deposited into and quantitized by a protein analyzer.

15. A method as defined in claim 14, in which the effluent is deposited into and quantitized by a hydrocarbon analyzer.

16. A method as defined in claim 11, including the step of comparing the estimated number of diopters of treatment accomplished to a desired number of diopters.

17. A method as defined in claim 16, including the step of modifying the laser surgery based upon the computation of estimated number of diopters of treatment accomplished compared to the desired number of diopters of treatment.

18. A method for increasing the accuracy and safety of ablative laser treatments, comprising the steps of:

providing an ablative laser;

removing an amount of tissue from the cornea, using the ablative laser, thereby providing an effluent;

aspirating the effluent;

quantitizing the effluent;

computing an estimated actual optical change based upon input data relating to a dimension of the ablated cornea and data related to the quantitized effluent;

comparing the estimated optical change to a desired optical change; and modifying the laser treatment based upon the comparison of the estimated actual optical change to the desired optical change.

19. A method as defined in claim 18, in which the effluent is quantitated in a protein analyzer.

20. A method as defined in claim 18, in which the input data relating to a dimension of the ablated cornea comprises input data relating to at least one of the radius, diameter, area and periphery of the ablated cornea.

21. A method as defined in claim 18, in which the actual optical change is computed by a computer using an algorithm based upon the Munnerlyn formula.

22. A method as defined in claim 18, in which the effluent is quantitated in a chemical analyzer.

23. A method as defined in claim 22, in which the effluent is quantitated in a hydrocarbon analyzer.

* * * * *